United States Patent [19]

Simpson et al.

[11] Patent Number: 5,265,621
[45] Date of Patent: Nov. 30, 1993

[54] APPARATUS FOR SAMPLING BLOOD

[76] Inventors: Shawn L. Simpson, 3706 Woodmont St., Toledo, Ohio 43613; Steven E. Young, 1249 Winding Way, Temperance, Mich. 48182

[21] Appl. No.: 861,300

[22] Filed: Mar. 31, 1992

[51] Int. Cl.$^5$ .............................................. A61B 5/00
[52] U.S. Cl. ................................... 128/764; 128/766
[58] Field of Search .............. 128/760, 765, 763, 766, 128/768, 771, 764; 604/184, 186, 187, 199, 207, 208, 210, 218, 220, 231, 121, 119, 118

[56] References Cited

U.S. PATENT DOCUMENTS

| | | | |
|---|---|---|---|
| 2,845,066 | 7/1958 | Hoppe | 604/184 |
| 4,153,186 | 5/1979 | Nye | 222/378 |
| 4,257,426 | 3/1981 | Bailey | 128/766 |
| 4,444,335 | 4/1984 | Wood et al. | 222/43 |
| 4,642,102 | 2/1987 | Ohmori | 604/210 |
| 4,643,200 | 2/1987 | Jennings et al. | 128/763 |
| 4,690,154 | 9/1987 | Woodford et al. | 128/765 |
| 4,758,232 | 7/1988 | Chak | 604/220 |
| 4,838,855 | 6/1989 | Lynn | 604/49 |
| 4,840,616 | 6/1989 | Banks | 604/110 |
| 5,002,066 | 3/1991 | Simpson et al. | 128/760 |
| 5,048,537 | 9/1991 | Messinger | 128/673 |
| 5,174,301 | 12/1992 | Sarstedt | 128/765 |

*Primary Examiner*—Stephen C. Pellegrino
*Assistant Examiner*—Guy V. Tucker
*Attorney, Agent, or Firm*—Marshall & Melhorn

[57] ABSTRACT

An apparatus for taking a blood sample after a catheter has been inserted into a patient including a syringe-type apparatus provided with a control collar which cooperates with radially extending portions of the plunger to selectably fix the axial position of the plunger. Retainer means is provided to prevent total withdrawal of the plunger from the syringe body. The plunger of the syringe may be provided with a center bore to permit flow of saline solution through the syringe to the patient.

12 Claims, 3 Drawing Sheets

APPARATUS FOR SAMPLING BLOOD

BACKGROUND OF THE INVENTION

This invention relates to an apparatus for sampling blood, and more particularly, to an apparatus to be integrally mounted in the tubing of a blood pressure monitoring system for safely and efficiently obtaining blood samples from patients.

In intensive care units, trauma units, and other medical facilities at hospitals, a catheter inserted into an artery of the patient is used for continuously monitoring blood pressure and obtaining blood samples. These patients typically have poor arterial access, are clinically unstable, and require continuous monitoring. Frequent blood sample analysis is also required.

When a patient has an arterial catheter, all blood samples tend to be drawn by accessing the line from the catheter to the monitoring devices rather than puncturing the patient's skin with a needle each time a blood sample is required. Drawing the blood samples from the arterial line is less painful for the patient and more convenient for the medical personnel.

A number of techniques are currently used for drawing blood from arterial lines. The existing techniques have not achieved the results desired by the medical staff and patients. In several systems, a significant portion of the blood drawn from the patient must be discarded in attempts to obtain a pure sample. The frequency of blood drawing and the amounts being drawn can pose a significant problem for certain patients, especially the elderly and the very young.

Infection is another serious problem with the existing techniques for drawing blood. Any break in the skin of the patient or any breaks in the monitoring system connected to the catheter serve as portal of entry for bacteria. The blood sampling systems currently in use provide a portal of entry for bacteria.

In recent years, medical personnel have faced a significant risk of contracting blood borne infections when using needles and in the general handling of the blood. Improved blood drawing systems are needed to reduce the chance of needle sticks and to eliminate any blood spillage.

The most common method for withdrawing blood from pressure monitoring lines involves the use of stopcocks and syringes. The stopcock is placed approximately 12 inches from the insertion site in series with a catheter, a transducer on the pressure monitoring system, and a saline supply. A port disposed on the side of the stopcock is used for blood sampling.

When the stopcock is turned to open the side port, the saline supply is temporarily stopped. A syringe is used to withdraw the saline and small amounts of blood from the tube and the catheter. Once the blood is drawn through the catheter and the tube to the side port of the stopcock, a second, heparinized syringe is inserted to withdraw the sample of blood. The stopcock is then turned to block the flow from the catheter and open the flow to the saline solution to flush out the side port. The stopcock is turned again to block the side port and connect the saline supply to the catheter, and to continue monitoring the blood pressure of the patient.

The stopcock system requires a number of manipulative steps in order to obtain the blood sample. The opening of the side port increases the possibility of contamination and infection of the patient's blood. Blood usually drips from the side port after the sample is drawn and blood residue may remain on the side port, even after the saline flush of the interior of the side port.

Other methods for obtaining a blood sample include T-connectors or rubber injection ports at the catheter insertion site. These systems can also result in a dilution of the blood sample. Dilution of the sample leads to inaccurate results. The tendency is to repeat the sampling and testing procedures, which increases the costs, time, risk of contamination, and patient blood loss.

Medical personnel desire an improved means for drawing blood samples because of the large amount of blood drawn daily and the potential problems associated with blood drawing.

SUMMARY OF THE INVENTION

In accordance with the present invention, there is provided a blood sampling apparatus to be installed as an integral part of the tubing extended from a catheter to a blood pressure monitoring system.

A first tube connected to the catheter extends to a syringe. The tube includes an in-line sampling port between the catheter and the syringe. The syringe contains a plunger with a center bore extending the full length of the plunger to permit the passage of fluid from one end of the syringe to the other end.

A second tube connected to the plunger in the syringe extends to the pressure transducer of the blood pressure monitoring system. The pressure transducer is connected to a flush valve assembly and a source of saline solution.

When monitoring blood pressure, the system is filled with saline solution from the pressure transducer through the syringe to the catheter. Variations in blood pressure are communicated through this static column of saline solution from the blood vessel to the transducer of the monitoring system.

To take a blood sample using this system, the plunger of the syringe is withdrawn such that the negative pressure draws the saline solution from the first tube into the body of the syringe and draws the blood of the patient from the blood vessel through the catheter into the first tube. The first tube, the syringe, and the sampling port are positioned such that blood is drawn past the sampling port but does not reach the syringe.

The blood sample is withdrawn through the sampling port. After the sample is withdrawn, the saline is forced back through the tube to the patient. The flush valve assembly is used to wash any blood back to the patient and prevent clotting in the tube.

An object of the present invention is provide a system for taking samples of blood from a blood pressure monitoring apparatus which substantially entirely eliminates the chance of exposing the patient to contamination and bacterial infection from the sampling process.

Another object of the present invention is to provide a system for taking samples of blood from a blood pressure monitoring apparatus which substantially entirely eliminates the chance of inadvertently contaminating the area around the patient with blood from the sampling process, decreasing the risk to medical personnel of contracting a blood-borne infection.

Another object of the present invention is to provide a means for drawing a blood sample from a blood pressure monitoring apparatus which provides means for timely termination of the blood drawing procedure and restoring an accurate pressure signal to the pressure transducer.

Another object of the present invention is to provide a more efficient system for drawing blood. The present invention is designed to reduce the amount of blood wasted in drawing an undiluted sample. In addition, the system is designed for the convenience of the medical personnel from an operational efficiency standpoint.

Another object of the present invention is to reduce the cost to the hospital and to the patient in taking a blood sample from blood pressure monitoring apparatus. Costs may be reduced when using the present invention because the system is easy to use, requires fewer components than the most common method of taking blood samples, and a majority of the required parts are mounted in-line and are reusable.

BRIEF DESCRIPTION OF THE DRAWINGS

The above, as well as other advantages of the present invention, will become readily apparent to those skilled in the art from the following detailed description of a preferred embodiment when considered in the light of the accompanying drawings in which.

DESCRIPTION OF THE PREFERRED EMBODIMENT

Figure 1:
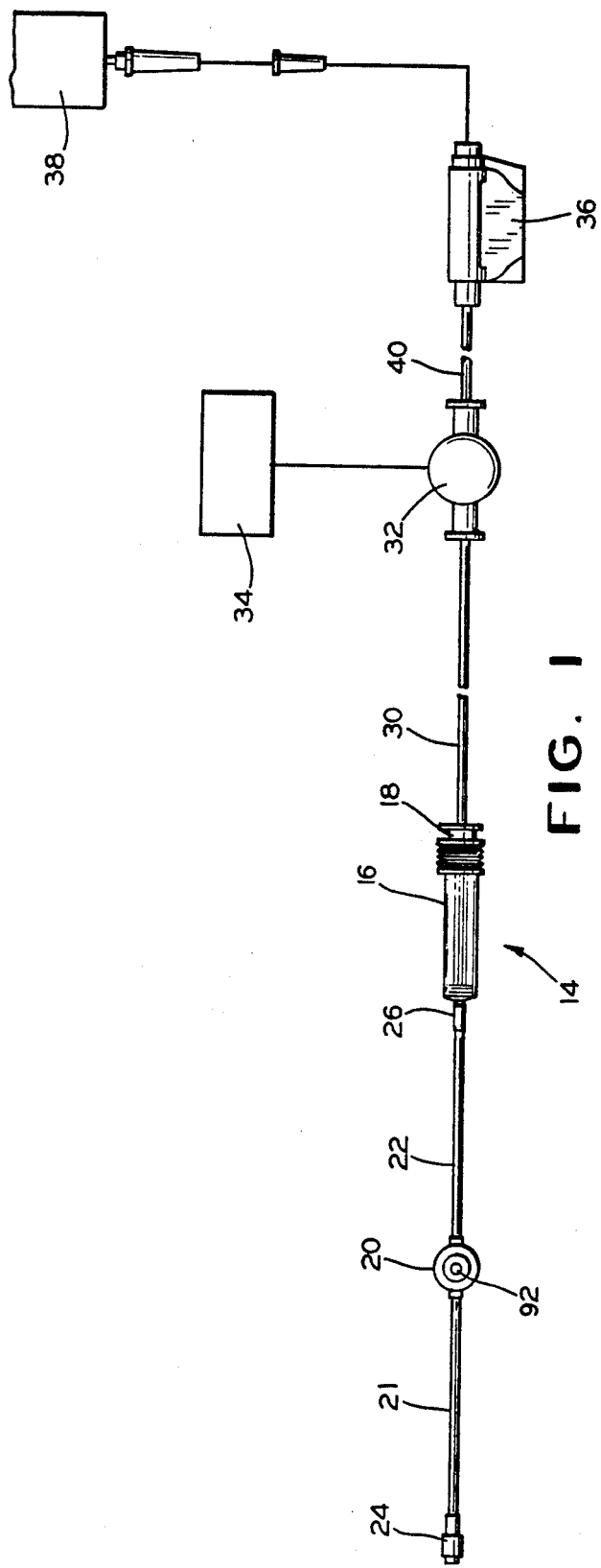
FIG. 1 is a schematic view of a system embodying the apparatus for sampling blood of the present invention.

Referring now to the drawings, there is shown in FIG. 1 a schematic view of the blood sampling apparatus for use with a typical hospital blood pressure monitoring system. A syringe 14, including a syringe body 16 and a plunger 18, is connected to the saline line used to monitor the patient's blood pressure, at a location between a sampling port 20 and a source of saline solution 38.

A first tube 21 is coupled to a standard coupling 24 at one end for connection to a catheter (not shown) for insertion into a patient's blood vessel. The other end of the first tube 21 is connected to a sampling port 20. A second tube 22 is affixed to the other side of the sampling port 20, and is in fluid communication with the first tube 21 through the sampling port 20. The other end of the second tube 22 is connected by a coupling 26 to one end of the syringe body 16. The plunger 18 inside the syringe body 16 has a full length center bore 28, as is clearly illustrated in FIGS. 4 and 6. A third tube 30 is affixed in the center bore 28 of the plunger 18, and is in fluid communication with the second tube 22 through the syringe 14.

The third tube 30 extends from the plunger 18 to a pressure transducer 32 which is electrically connected to a monitor 34 which displays and records variations in a patient's blood pressure. The pressure transducer 32 is also connected through a tube 40 to a flush valve assembly 36 and a source of saline solution 38. The flush valve assembly 36 includes a capillary tube to provide a steady drip of saline solution to the associated catheter. The flush valve assembly 36 also includes a bypass valve to provide a larger flow of saline to flush the tube 40, the tube 30, the tube 22, and the tube 21.

The tubes 21, 22, and 30 from the catheter to the pressure transducer 32 are normally filled with a saline solution. The saline solution forms a static column between the patient's blood vessel and the pressure transducer 32 whereby variations in blood pressure are sensed by the pressure transducer 32 and the associated monitor 34.

When a blood pressure monitoring system is coupled to a patient, it is customary to provide means for periodically drawing a blood sample from the patient. The blood sampling apparatus of the present invention provides both the necessary communication between the catheter and the pressure transducer 32 and the means for drawing a blood sample.

Figure 2:
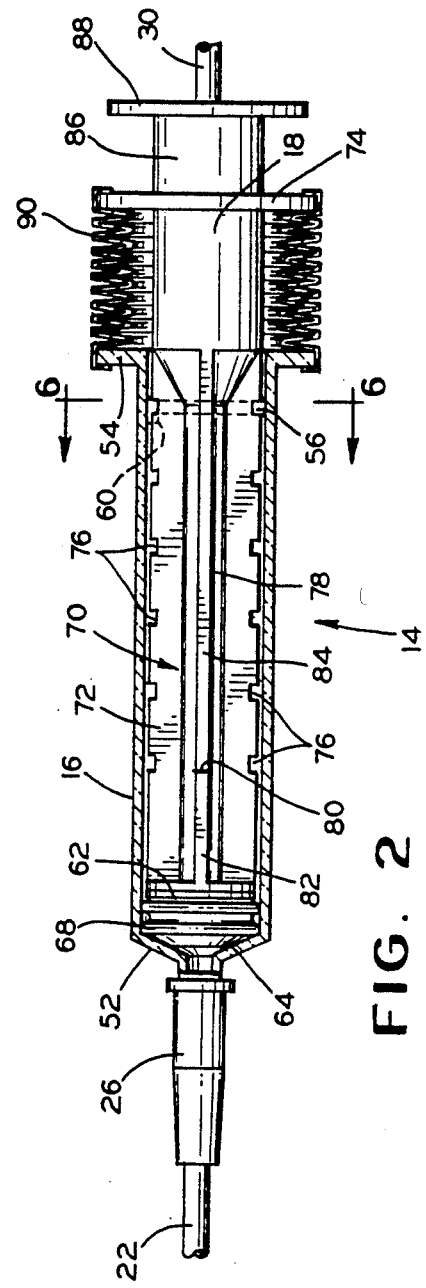
FIG. 2 is a side view, partly in cross section, of the syringe body and plunger of the apparatus illustrated in FIG. 1.
Figure 3:
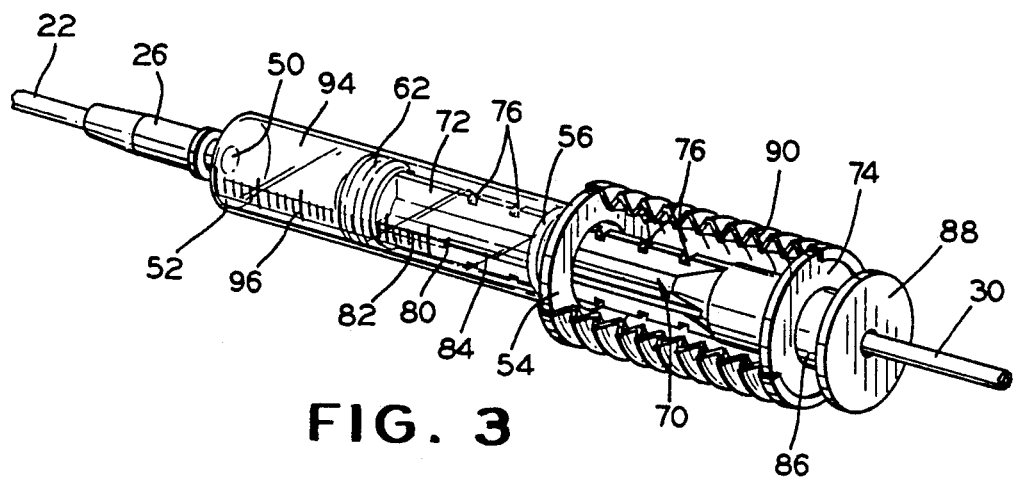
FIG. 3 is a perspective view of the syringe body and plunger illustrated in FIG. 2 with portions cut-away to more clearly illustrate the structure.

As shown in FIGS. 2 and 3, the second tube 22 is connected by a coupling 26 to an aperture 50 in a conical end 52 of the syringe body 16. The syringe body 16 is tubular in shape for receiving the plunger 18. The other end of the syringe body 16 is open and a radially outwardly extending flange 54 is formed at the open end.

The syringe body 16 is also provided with a control collar 56 which is spaced axially inwardly from the open end of the syringe body 16 and extends radially inwardly from the inner surface of the syringe body 16. The control collar 56 has two slots 58, as clearly illustrated in FIG. 6, on opposite sides of the control collar 56 for guiding and positioning the plunger 18 as it is moved axially within the syringe body 16.

Figure 4:
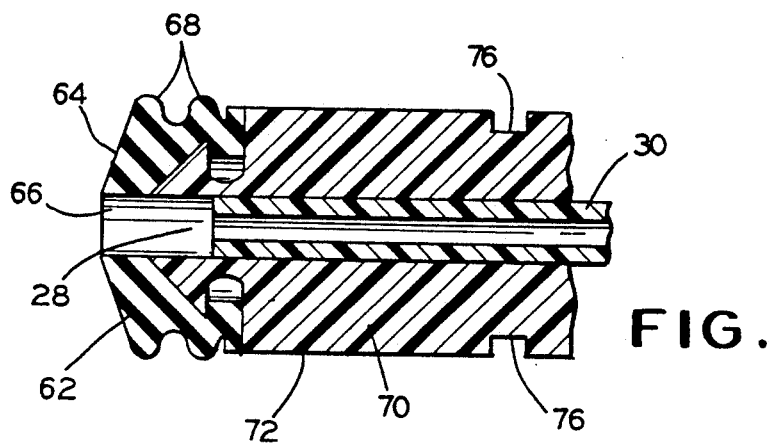
FIG. 4 is an enlarged fragmentary sectional view of one end of the plunger of the apparatus illustrated in FIGS. 2 and 3.

As shown in FIG. 2, the plunger 18 includes a seal 62 affixed to the end of the plunger 18 inserted into the syringe body 16. The end surface 64 of the seal 62 engages the conical end 52 of the syringe body 16 when the plunger 18 is fully inserted. As shown in FIG. 4, the end surface 64 is provided with an aperture 66 which is aligned with the center bore 28 of the plunger 18. A pair of circumferential ridges 68 on the seal 62 slidingly engage the inner surface of the syringe body 16.

Figure 5:
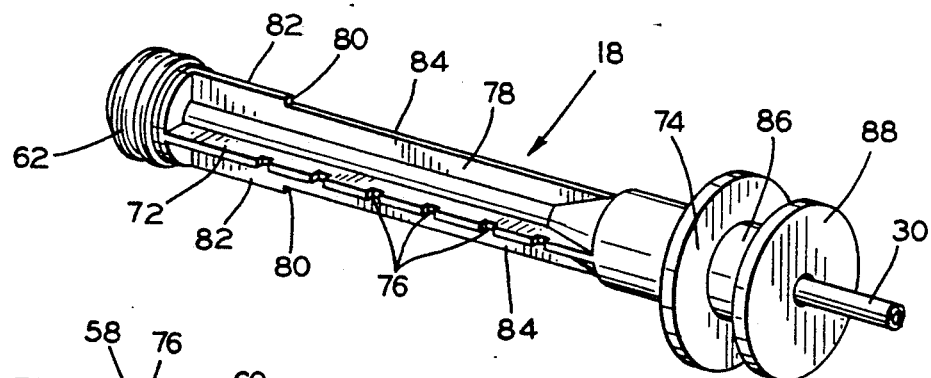
FIG. 5 is a perspective view of the plunger of the apparatus illustrated in FIGS. 2 and 3.
Figure 6:
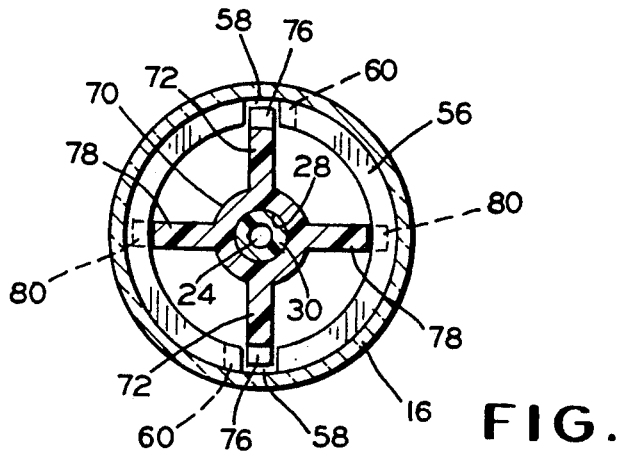
FIG. 6 is a sectional view of the apparatus taken along line 6—6 of FIG. 2.

As shown in FIGS. 5 and 6, the body 70 of the plunger 18 includes a pair of guide ribs 72 located on opposite sides of the plunger body 70. The guide ribs 72 extend axially from the seal 62 to the flange 74 on the other end of the plunger 18. The guide ribs 72 are retained in the slots 58 of the control collar 56 to guide axial movement and restrict rotational movement of the plunger 18 in the syringe body 16.

An identical set of notches 76 is spaced along the outer edge of the guide ribs 72. When the plunger 18 is moved to a position in the syringe body 16 such that a notch 76 in each of the guide ribs 72 is located in the slots 58 and aligned with the control collar 56, the plunger 18 may be rotated to position the control collar 56 within the notch 76 thereby fixing the axial position of the plunger 18. A stop 60 is formed adjacent to each of the slots 58 and extends perpendicular to the control collar 56 along the inner surface of the syringe body 16 towards the conical end 52. The stops 60 allow the plunger 18 to be rotated in only one direction (counterclockwise) when the notches 76 are positioned in the slots 58.

The plunger 18 may be rotated in a counterclockwise direction until the guide ribs 72 contact the stops 60 to limit further rotation. Once the notches 76 are positioned in the slots 58 and the plunger 18 is rotated, axial movement of the plunger 18 in the syringe body 16 is not possible until the plunger 18 is rotated in a clockwise direction back to the position where the guide ribs 72 are aligned with the slots 58.

The plunger body 70 also includes a pair of axial retainer ribs 78 located on opposite sides of the plunger body 70 at approximately 90 degrees from the guide ribs 72. The outer edge of each retainer rib 78 has one step 80 near the seal 62 which divides the retainer ribs 78 into an upper segment 82 towards the seal 62 and a lower segment 84 towards the other end of the plunger 18. When the plunger 18 is moved axially within the syringe body 16, the lower segment 84 does not engage the control collar 56. The upper segment 82 is in close proximity to the inner surface of the syringe body 16. With the guide ribs 72 aligned with slots 58 to allow the plunger 18 to be withdrawn, the steps 80 will engage the control collar 56 to prevent the total withdrawal of the plunger 18 from the syringe body 16.

The head 86 of the plunger 18, on the end opposite of the seal 62, extends past the flange 54 of the syringe body 16. The head 86, which always remains external to the syringe body 16, is a tubular segment having a first flange 74 and an axially spaced second flange 88 extending radially outward from the head 86 of the plunger 18. Medical personnel using the syringe 14 may grasp the plunger 18 at flange 88 and move the plunger 18 within the syringe body 16 by pushing, pulling, or rotating the plunger 18 while restraining the syringe body 16.

Without additional provisions, the interior components of syringe 14 would be exposed to bacteria and other contaminants in the ambient environment when the plunger 18 is operated. As shown in FIGS. 2 and 3, in order to maintain sterile conditions, an expandable sleeve 90 with accordion-style pleats is sealably attached to the flange 54 of the syringe body 16 and the first flange 74 on the head 86 of the plunger 18. When the plunger 18 is fully inserted, the sleeve 90 is compressed. When the plunger 18 is withdrawn, the sleeve 90 expands to prevent exposure of the plunger body 70 and other internal components of the syringe 14 to contaminants in the environment.

In addition to expanding and contracting in a axial direction when the plunger 18 is inserted or withdrawn, the sleeve 90 must also be able to maintain the sterile conditions when the plunger 18 is rotated to fix the plunger 18 in a desired axial position. If the sleeve 90 is affixed to the flange 74 of the plunger 18, then the sleeve 90 may be made of an elastic material, such as latex, to accommodate the rotational movement of the plunger 18 relative to the syringe body 16. The sleeve 90 may also have an overlapping segment under tension to slidingly engage the flange 74 of the plunger 18. This arrangement maintains sterile conditions and allows the plunger 18 to rotate independent of the sleeve 90.

As shown in FIG. 1, the sampling port 20 is connected between the first tube 21 and the second tube 22. The sampling port 20 typically includes a self-sealing latex cap 92 in an aperture into the sampling port 20. The latex cap 92 is effective to prevent both contamination of the blood from outside sources and leakage of the blood outside the sampling port 20. A dull point needle of a sampling syringe (not shown) can be inserted through the latex cap 92 to withdraw a blood sample. When the needle is removed from the latex cap 92, the cap 92 immediately reforms its shape to seal the aperture.

Once the apparatus of the present invention has been installed with a sampling port 20 between the catheter and the pressure transducer 32, medical personnel can safely and conveniently draw blood samples from the patient. The syringe 14 initially has the plunger 18 fully inserted when not drawing a sample to facilitate the functioning of the blood pressure monitoring system. Saline solution is passing from the third tube 30 through the second tube 22 and the first tube 21 to the catheter and patient. The fully inserted plunger 18 may be rotated to prevent unintentional axial movement of the plunger 18.

When a blood sample is needed, the medical staff person rotates the plunger 18 to line up the guide ribs 72 with the slots 58 and pulls the plunger 18 axially. The capillary tube in the flush valve assembly 36 is formed with a much smaller interior diameter than the interior diameters of the catheter, the sampling port 20, or the tubes 21 or 22, with the result that the negative pressure created in the syringe 14 tends to draw saline solution from the tubes 21 and 22 into the fluid storage area 94 of the syringe body 16 shown in FIG. 3. The notches 76 on the guide ribs 72 are spaced apart such that the axial position of the plunger 18 may be releasably fixed after a specific volume of saline solution is drawn into the syringe body 16. A gradient scale 96 on the syringe body 16 confirms the amount of saline solution drawn into the fluid storage area 94.

As the saline is drawn from the tubes 21 and 22, an equivalent amount of blood is drawn from the patient into tubes 21 and 22. The lengths and interior diameters of tubes 21 and 22 are selected to place sampling port 20 in optimal relationship with the syringe 14 and the catheter to achieve the best sampling results. The blood drawn from the sampling port 20 will be relatively pure blood with very little dilution.

After the blood is drawn, the plunger 18 is fully reinserted into the syringe body 16 to force the saline back into tubes 21 and 22. The flush valve assembly 36 is operated to flush any blood residue in the sample port 20 or tubes 21 or 22 back to the patient. The column of saline solution is restored and the blood pressure system is operational.

Maintaining clean and sterile conditions in and about the blood sampling apparatus is very important. The sleeve 90 about the plunger 18 improves the sterility of the syringe 14. The steps 80 on the retainer ribs 78 cooperate with the control collar 56 to prevent the plunger 18 from being removed from the syringe body 16. Additionally, the syringe 14 is positioned at a predetermined distance from the catheter such that blood from the patient may be drawn into the first tube 21, past the sampling port 20, and partially into the second tube 22. The syringe 14 is preferably sized so that it cannot draw blood into the syringe body 16 to contaminate the seal 62 and the syringe body 16. If the syringe 14 is utilized with tubes 21 or 22 of smaller diameter, or shorter length than is optimal, blood might be drawn into the syringe body 16, contaminating the seal 62 and the syringe body 16. The preferred embodiment therefore provides for intermediate notches 76 spaced apart on the guide ribs 72 of the plunger body 70 to allow the plunger 18 to be fixed in an intermediate axial position after sufficient saline solution had been drawn into the syringe 14 to draw blood past the sample port 20, but not into the syringe 14.

The blood sampling apparatus of the present invention provides improved sterility to the patient and reduces the exposure of the medical personnel to the blood of the patient. The apparatus is efficient and convenient to use and relatively inexpensive to manufacture, which helps to reduce hospital costs without sacrificing patient care. The in-line orientation of the syringe 14 is not overly susceptible to becoming entangled with other materials or objects.

Figure 7:
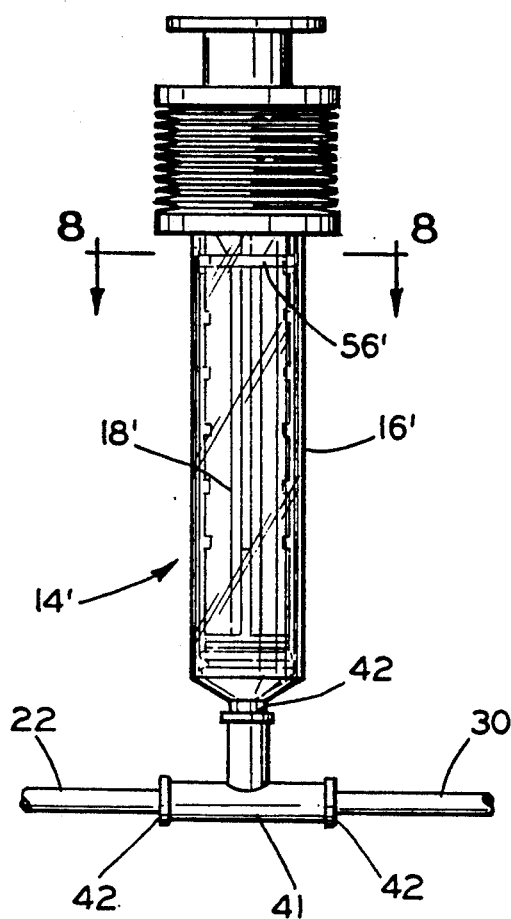
FIG. 7 is a elevational view of an alternate embodiment of apparatus embodying the features of the present invention in a system similar to the system illustrated in FIG. 1.
Figure 8:
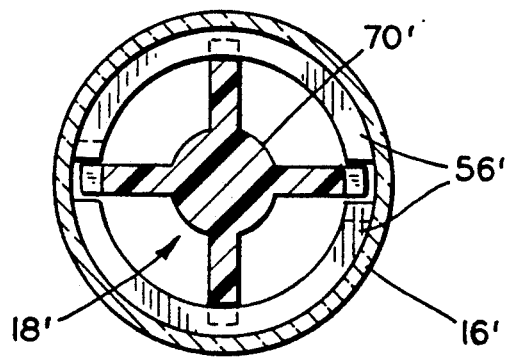
FIG. 8 is a sectional view of the syringe body and plunger taken along line 8—8 of FIG. 7.

In FIGS. 7 and 8, another embodiment of the present invention is shown which would utilize a multiport connection (e.g., a "T" or "Y" connection) 41 in the tubing between the sampling port 20 and the pressure transducer 32, connecting the second tube 22 and the third tube 30 via connection points 42. A syringe 14' fixably engaging the multiport connection 41 at the remaining connection point 42 is substantially similar to that described above as the preferred embodiment, except that the plunger 18' possesses no center bore 28. The plunger 18' may be selectably fixed at various points in its range of axial movement by rotating it to engage the control collar 56' as previously described. Withdrawing the plunger 18' would create a negative pressure between the second tube 22 and the third tube 30, tending to draw in saline solution from the first tube 21 and the second tube 22, which in turn would draw blood from the patient through the first tube 21, past the sample port 20, and partially into the second tube 22, enabling a sample to be obtained.

In accordance with the provisions of the patent statutes, the present invention has been described in what is considered to represent its preferred embodiment. However, it should be noted that the invention can be practiced otherwise than as specifically illustrated and described without departing from its spirit or scope.

What is claimed is:

1. An apparatus for taking a blood sample from a patient after a catheter has been inserted into the patient, said apparatus comprising:
    a) an elongate hollow syringe body including an open end, a closed end having an aperture, and an inner surface;
    b) a plunger adapted to be slidably positioned within said syringe body to define a variable volume reservoir, said plunger including means for providing a fluid tight seal between an outer surface of said plunger and the inner surface of said syringe body, and a full-length longitudinal center bore in fluid communication with the variable volume reservoir;
    c) retention stop formed on said plunger for retaining said plunger within said syringe body;
    d) a first tubular means for providing fluid communication between a catheter in the patient and said aperture in said syringe body;
    e) a second tubular means for providing fluid communication between the bore of said plunger and a source of saline solution whereby continuous fluid communication from the source of saline solution to the catheter in the patient is achieved; and
    f) a sampling port in fluid communication with said first tube and spaced apart from said syringe body and the catheter, whereby the partial withdrawal of said plunger from said syringe body causes a volume of saline solution to flow from said first tube into said syringe body and a volume of blood to flow from the patient into said first tube for aspiration of the blood sample from said first tube through said sampling port.

2. The blood sampling apparatus defined in claim 1 including a means for monitoring blood pressure connected to said second tube whereby blood pressure may be continuously monitored.

3. The blood sampling apparatus defined in claim 1 including an expandable, fluid-tight sleeve connected between the open end of said syringe body and said plunger.

4. The blood sampling apparatus defined in claim 3 wherein said sleeve includes extensible and flexible accordion pleats.

5. The blood sampling apparatus defined in claim 3 wherein said sleeve is made of latex material.

6. The blood sampling apparatus defined in claim 1 wherein said syringe body includes a locking means for selectively limiting longitudinal movement of said plunger.

7. The blood sampling apparatus defined in claim 6 wherein said syringe body includes a second locking means for limiting rotational movement of said plunger in said syringe body.

8. The blood sampling apparatus defined in claim 1 including means for defining a plurality of selected reservoir volumes for storing the saline solution communicated from said first tube to the variable volume reservoir in said syringe body during withdrawal of said plunger.

9. The blood sampling apparatus defined in claim 8 wherein said plunger includes at least one longitudinal guide rib and said syringe body includes a control collar adjacent to the open end of said syringe body and extending radially inward, the control collar having a slot for each guide rib such that the guide rib is aligned in the slot of the control collar during longitudinal positioning of said plunger.

10. The blood sampling apparatus defined in claim 9 wherein the guide rib includes a plurality of spaced apart notches whereby the plunger is selectively locked in position by the rotational positioning of the control collar in said notches, said plunger defining a selected reservoir volume within said syringe body.

11. The blood sampling apparatus defined in claim 1 including a retainer means for retaining said plunger in said syringe body.

12. An apparatus for taking a blood sample from a patient after a catheter has been inserted into the patient and connected to a blood pressure monitoring system, said apparatus comprising:
    a) an elongate hollow syringe body including an open end, an inner surface, a closed end provided with an aperture, and a control collar adjacent to the open end and extending radially inward;
    b) a plunger adapted to be slidably positioned within said syringe body to define a variable volume reservoir, said plunger including a full-length longitudinal center bore in fluid communication with the variable volume reservoir, an internal end having a seal for engaging an inner surface of said syringe body, an external end extending from the open end of said syringe body and having means for longitudinally positioning said plunger, and at least one longitudinal guide rib aligned in the control collar and having a plurality of notches for selectively locking said plunger;
c) retention stop formed on said plunger for retaining said plunger within said syringe body;
d) an extensible and flexible sterile sleeve sealably connected between the open end of said syringe body and the external end of said plunger;
e) a first tube for providing fluid communication between a catheter in the patent and said aperture in said syringe body;
f) a second tube for providing fluid communication between the bore of said plunger and a source of saline solution whereby continuous fluid communication from the source of saline solution to the catheter in the patient is achieved; and
g) a sampling port in fluid communication with said first tube and spaced apart from said syringe body and the catheter, whereby the longitudinal withdrawal and rotational locking of said plunger in said syringe body causes the sterile sleeve to expand, a volume of saline solution to flow from said first tube into said syringe body, and a volume of blood to flow from the patient into said first tube for aspiration of the blood sample from said first tube through said sampling port.

* * * * *